(12) United States Patent
Sanchez et al.

(10) Patent No.: US 8,887,554 B2
(45) Date of Patent: Nov. 18, 2014

(54) RAW PROPORTIONAL TOXIC SAMPLER FOR SAMPLING EXHAUST

(75) Inventors: Lawrence James Sanchez, Ann Arbor, MI (US); Joseph McDonald, Ann Arbor, MI (US); Charles Schenk, Dexter, MI (US)

(73) Assignee: The United States of America as represented by the Administrator of the U.S. Environmental Protection Agency, Washington, DC (US)

( * ) Notice: Subject to any disclaimer, the term of this patent is extended or adjusted under 35 U.S.C. 154(b) by 412 days.

(21) Appl. No.: 13/451,587

(22) Filed: Apr. 20, 2012

(65) Prior Publication Data

US 2013/0276552 A1 Oct. 24, 2013

(51) Int. Cl.
  *G01N 33/00* (2006.01)
(52) U.S. Cl.
  USPC .......................................... 73/23.31
(58) Field of Classification Search
  CPC ............................ G01M 15/102; G01N 1/2252
  USPC .......................................... 73/23.31, 863.03
  See application file for complete search history.

(56) References Cited

U.S. PATENT DOCUMENTS

| | | | | |
|---|---|---|---|---|
| 4,657,737 | A * | 4/1987 | Kampelmuhler | 422/94 |
| 5,546,788 | A * | 8/1996 | Dickow | 73/28.01 |
| 6,112,574 | A * | 9/2000 | Hirano et al. | 73/23.31 |
| 6,176,125 | B1 * | 1/2001 | Hirano et al. | 73/114.69 |
| 6,470,732 | B1 * | 10/2002 | Breton | 73/23.31 |
| 7,297,549 | B2 * | 11/2007 | Lanier et al. | 436/175 |
| 7,389,703 | B2 * | 6/2008 | Wei et al. | 73/863.03 |
| 7,637,144 | B2 * | 12/2009 | Hodzic et al. | 73/23.31 |
| 2008/0022752 | A1 * | 1/2008 | Hodzic et al. | 73/23.31 |
| 2008/0141757 | A1 * | 6/2008 | Atkinson et al. | 73/23.31 |

\* cited by examiner

*Primary Examiner* — John Fitzgerald
(74) *Attorney, Agent, or Firm* — Bacon & Thomas, PLLC

(57) ABSTRACT

Components of interest are captured on a resin column from a sample of exhaust gas from an operating vehicle. Makeup air is added to the residual exhaust gas flow exiting the resin column at a junction downstream of the resin column. Makeup air flow rate is determined using a laminar flow element and pressure and temperature gauges associated therewith. The sample and the makeup air are drawn together through a blower and the flow rate through the blower is calculated based on differential pressure across the blower and temperature of the gas drawn through the blower. The controller adjusts a proportional control valve in the makeup air line to regulate the sample flow rate, taken as the blower flow rate minus the makeup air flow rate, at a predetermined proportion of the exhaust gas flow rate.

4 Claims, 3 Drawing Sheets

RAW PROPORTIONAL TOXIC SAMPLER FOR SAMPLING EXHAUST

BACKGROUND OF THE INVENTION

1. Field of the Invention

The present invention provides mobile emission measurement with proportional sampling of vehicle raw exhaust to collect a number of different emissions or toxic compounds in the vehicle exhaust gas.

2. The Prior Art

A need has existed in the art for measurement of polycyclic aromatic hydrocarbons ("PAHs" and "nitro-PAHs") from a vehicle during a transient test schedule. This data is needed to determine effects on health of exhaust components from engines run on gasoline and various ethanol blends.

A number of prior art devices and methods provide steady state sampling. However, a need exists for transient sampling.

The prior art bagged mini diluter is a proportional sampler but the volume that it draws is too small. Also, it dilutes the sample before it is collected which is not desirable when measuring PAHs from modern spark ignited engines due to the low concentration of PAHs in their exhaust.

Particulate matter (PM) samplers also pull a proportional sample but, if pulling from a Constant Volume System (CVS), the flow to which that sample is proportional, is very steady. While PM samplers that pull from exhaust which varies in flow rate are also known, the volume that such samplers pull out is too small.

SUMMARY OF THE INVENTION

An object of the present invention is to compile data for various exhaust components (toxic inventories) from engines over realistic engine operating conditions.

Another object of the present invention is to provide an apparatus which pulls a sample from the vehicle exhaust which is an order of magnitude larger than the exhaust sample pulled by the prior art bagged mini diluters and PM samplers.

To achieve the foregoing objectives the present invention provides an apparatus, i.e., a raw proportional toxic sampler (hereinafter "RPTS"), for capturing components, of interest, e.g. toxic components from the vehicle exhaust gas. The apparatus of the present invention includes: a sample tube or other means for capturing a sample of exhaust gas from an operating vehicle and introducing the captured sample into a sample line; a resin column connected to the sample line for receiving the exhaust gas sample and selectively capturing the components of interest on the resin, with a residual exhaust gas flow exiting the resin column; and a makeup air line for adding makeup air to the residual exhaust gas flow at a junction downstream of the resin column. A laminar flow element is provided in the air line, together with associated temperature and pressure sensors, for measuring the makeup air flow rate. A proportional control valve is also provided in the makeup air line for controlling the makeup air flow rate. A blower draws the sample through the sample line, draws the makeup air through the makeup air line and draws the combined flow of residual sample and makeup air through a blower inlet line. The apparatus further includes a controller for calculating the makeup air flow rate based on signals from the temperature and pressure sensors associated with the laminar flow element and for calculating the flow rate through the blower based on signals from temperature and pressure sensors associated with the blower. The controller outputs a signal controlling the proportional control valve to regulate the flow of makeup air so that the sample flow rate is maintained at a constant percentage of the exhaust gas flow rate. The sample flow rate is taken as the blower flow rate minus the makeup air flow rate.

The present invention also provides a method for capturing components of interest from the exhaust gas of an operating vehicle. The method includes measuring the exhaust gas flow rate and capturing a sample of the exhaust gas. A captured exhaust gas sample is passed through a resin column which serves to selectively capture the components of interest with output of a residual exhaust gas flow. The method further includes adding makeup air to the residual exhaust gas flow at a point downstream of the resin column, measuring the makeup air flow rate utilizing a laminar flow element and associated temperature and pressure elements, determining flow of the combined residual sample and makeup air through a blower and controlling the proportional control valve to regulate the makeup air flow rate to maintain the sample flow rate, taken as the blower flow rate minus the makeup air flow rate, as a set percentage of the exhaust gas flow rate.

An advantage of the RPTS of the present invention is its ability to sample a large volume of a vehicle's exhaust over a transient test schedule. The RPTS can pull up to 10% of the vehicle's exhaust.

DETAILED DESCRIPTION OF THE PREFERRED EMBODIMENTS

In the present invention the flow control hardware is downstream of where the sample is collected. This is important for measurement of certain constituents, dioxin for example, because many materials are catalysts for dioxin formation. Another advantage of the present invention is that the full sample train can be rinsed to prevent any loss of sample. When measuring polycyclic aromatic hydrocarbons (PAHs), nitro-polycyclic aromatic hydrocarbons (n-PAHs), dioxins and furans, the concentrations in the exhaust are very low compared to criteria pollutants, so preventing loss of sample is very important. In most prior art proportional samplers the mass flow controller comes in contact with the sample so that part of the sample train cannot be rinsed.

The sampler pulls and collects an undiluted raw sample. Because the concentrations of the constituents of interest are very low, diluting the sample would reduce the amount of sample collected.

The present invention controls flow by maintaining a relatively constant total flow through the system and varying the air to control the sample flow rate. Sample Flow Rate=Total Flow Rate−Makeup Air Flow Rate. By controlling the sample flow rate as the difference between total flow rate through the blower and the makeup air flow rate, the turn down ratio is much smaller than techniques and apparatus controlling the sample flow directly wherein the sample flow will vary from 5 slm to 250 slm, which is a 50:1 turn down ratio. In the present invention the valve that is controlling the flow is only controlling the flow between 50 slm to 500 slm, a 10:1 turn down ratio. Reducing the turn down ratio allows the flow meter to operate in a smaller range which increases the accuracy of the measurement across the flow range of the meter. Controlling the sample flow with the makeup air also increases the responsiveness of the sampler since a small change in the makeup air flow rate causes a relatively large change in sample flow rate.

The RPTS pulls a large proportional sample of vehicle exhaust and collects the constituents of interest in the exhaust on AMBERLITE® XAD-2° (trademarks of the Rohm & Haas Company) by measuring the total flow out of the sampler and controlling the makeup air to give the desired sample flow as a constant proportion (percentage) of the exhaust gas flow. Sample flow=Total flow−makeup air flow. The total flow is measured by using a positive displacement pump, with temperature measurement upstream and pressure measurement upstream and downstream of the pump. The makeup air flow is measured by using a Laminar flow element (LFE) with a deferential pressure gauge, absolute upstream pressure measurement and an upstream temperature measurement. The air is controlled using a proportional valve down-stream of the LFE. All the sensors are measured and filtered at 5 kHz. All calculations and control are done at 20 Hz.

Figure 1:
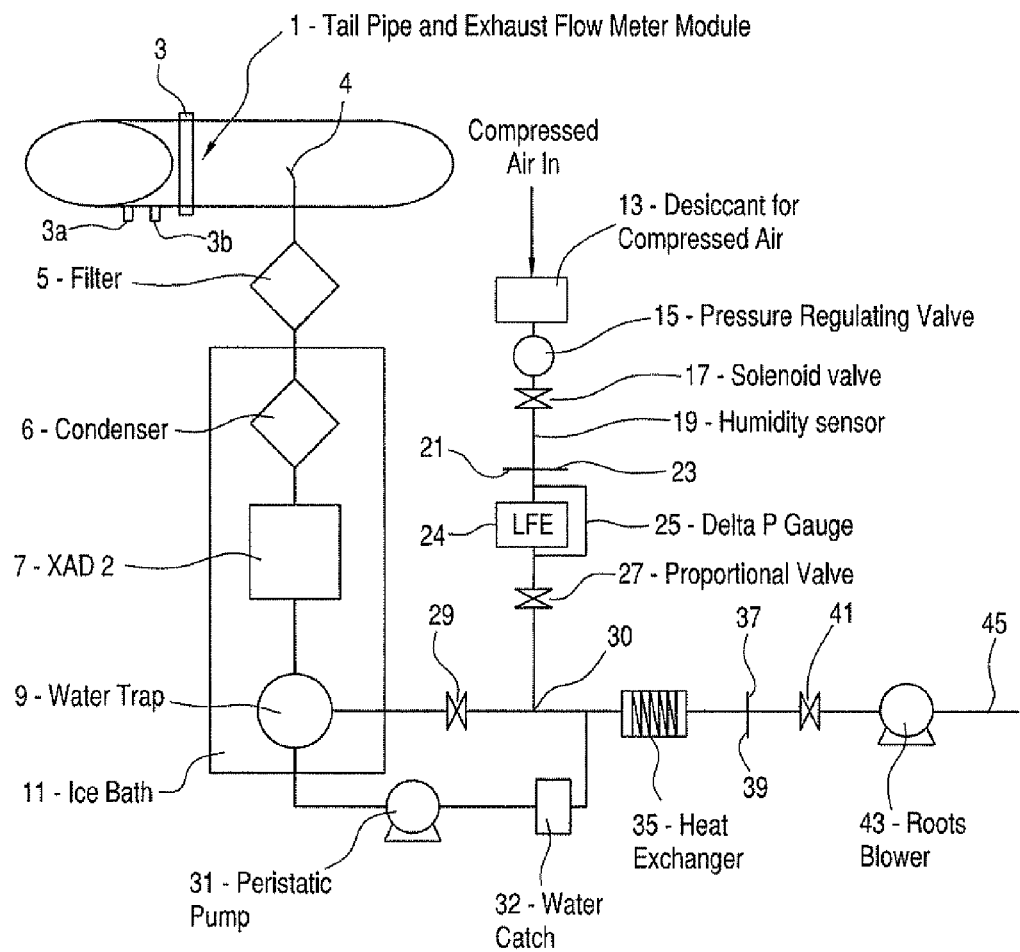
FIG. 1 is a schematic view of one embodiment of the apparatus of the present invention.
Figure 2:
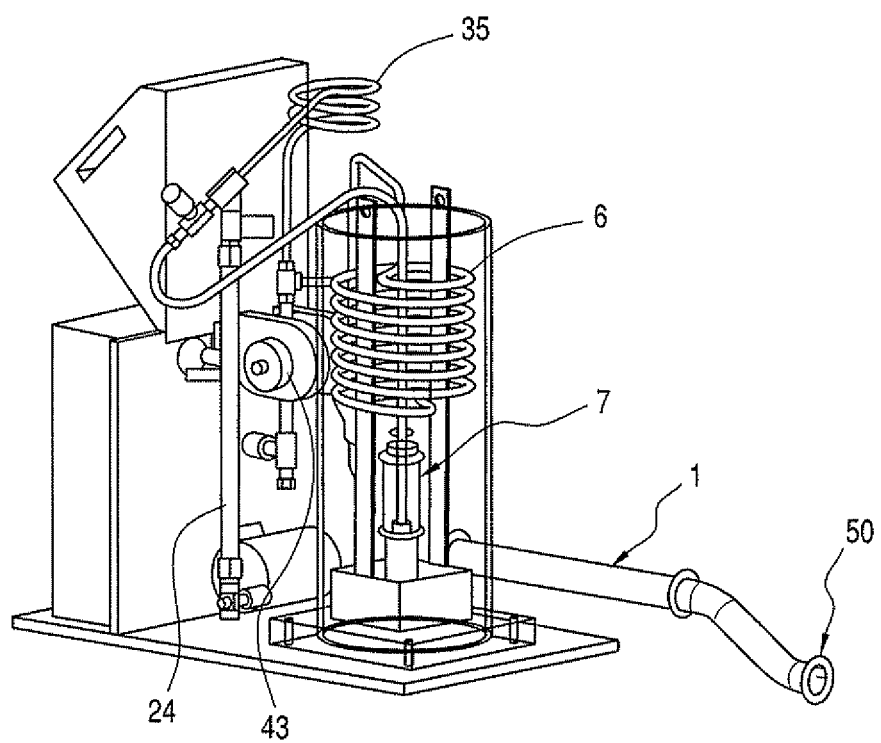
FIG. 2 is a perspective view of the apparatus of FIG. 1.
Figure 3:
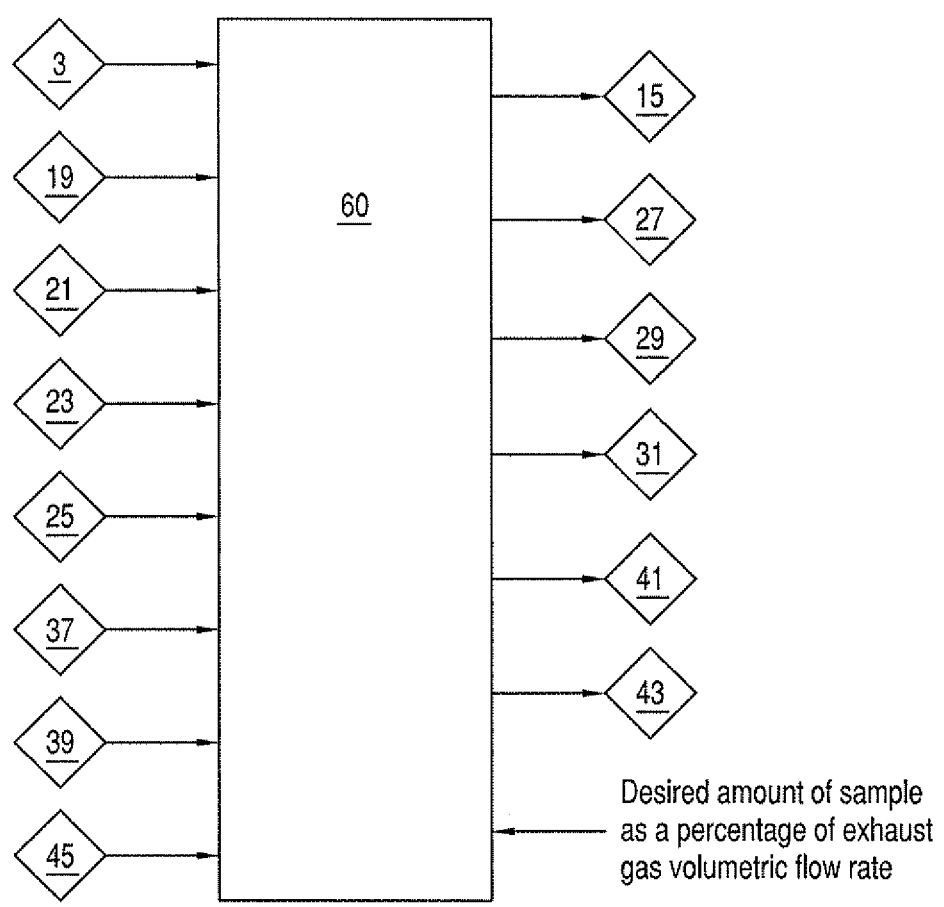
FIG. 3 is a schematic view of a controller for operation of the apparatus of FIG. 1

FIGS. 1 and 2 show one embodiment of the apparatus of the present invention. An exhaust gas flow meter module 1 is designed to be readily attached to and detached from the tailpipe of a vehicle powered by an internal combustion engine. The module 1 attaches to the vehicle exhaust through a connector pipe 50 (FIG. 3). The exhaust gas flow meter module 1 houses a flow meter element 3 and a sample tube 4, for example, as disclosed in U.S. Pat. No. 6,470,732, the teachings of which are incorporated herein by reference. One suitable flow sensing element 3 is manufactured by Dieterich Standard of Boulder, Colo., a subsidiary of Dover Industries, and is marketed under the trade name ANNUBAR™ DIAMOND II™ and is of the differential pressure type. The sample tube 4 extends from the exterior to approximately the center of the exhaust gas flow meter module 1 and has its distal end bent so that the sampling probe opening is facing upstream of the exhaust gas flow. Other embodiments calculate the exhaust flow based on intake air flow measurement and do not include an exhaust gas flow meter.

The sample collected through sample tube 4 is then routed through a filter or particulate trap 5, a condenser 6, and a column 7 which contains the aforementioned AMBERLITE® XAD-2® for collecting the exhaust gas components of interest. Upon exiting the resin column 7 the remaining exhaust gas passes through a water trap 9 from which water is removed by a peristatic pump 31 to a water catch 32. Note that the condenser 6, the resin column 7 and the water trap 9 are all contained within an ice bath 11. The ice bath 11 serves to cool the exhaust gas to a temperature of approximately 2-5 degrees C. so as to operate in the temperature range where the XAD-2® resin is very efficient in collecting the exhaust gas components of interest. Exiting the water trap 9, the exhaust gas passes through an open/shut valve 29 which is used to close off the sample train from the rest of the system for purposes of calibrating the blower 43 with the LFE 24.

Downstream of valve 29 makeup air is added to the exhaust gas at a junction 30 and the combined exhaust gas and makeup air is then passed through a heat exchanger 35, and valve 41 (used for leak checks) and, finally, to exhaust through a ROOTS® (trademark of Dresser Inc.) blower 43. The ROOTS® blower 43 serves to draw the exhaust gas sample and the makeup air through the system and operates at an approximately constant volumetric flow rate. The volumetric flow rate through the blower 43 is determined by calculation based on the rotational speed of the blower 43, pressure measurements upstream and downstream of the blower 43, by pressure sensors 37 and 45, and the temperature of the exhaust gas entering the blower 43 as measured by thermocouple 39.

Compressed air is introduced through a container of desiccant 13. Exiting the desiccant container 13, the makeup air passes through a regulator valve 15 which serves to set the desired pressure of air at the inlet of the laminar flow element 24. After exiting the regulator valve 15 the air passes through solenoid valve 17 which is used to close off the compressed air, for performing a leak check on the system. Exiting the solenoid valve 15, the humidity of the makeup air is determined by use of humidity sensor 19 to verify that all water has been removed from the compressed air. Operating parameters are detected by temperature sensor 21, the pressure sensor 23, and the delta P gauge 25, which measures pressure drop across the LFE 24, and are used in calculation of the volumetric flow rate of the makeup air. An LFE is used for measurement because of its high accuracy and short response time, as well as its ready availability in the market. From the LFE 24 the makeup air flows through a proportional control valve 27 which regulates the flow rate of the makeup air and thereby indirectly controls the volumetric flow rate of the sample at a constant percentage of the volumetric flow rate through the exhaust gas flow meter module 1.

While the volumetric flow rate of exhaust gas through module 1 will vary with the vehicle speed and load, the proportional control valve 27 serves to regulate the flow of makeup air to maintain the sample flow (volumetric flow rate) at an approximately constant proportion (percentage) of the exhaust gas flow through module 1. In other words, the amount of sample through 4 will remain at a constant percentage of the volumetric flow rate of the exhaust gas, even as the latter changes with vehicle speed and load.

The heat exchanger 35 serves to bring the mixed sample/makeup air to ambient temperature to thereby simplify the flow rate calculations for the total volumetric flow rate through the positive displacement blower 43.

Pressure sensors 37 and 45 measure the pressures upstream and downstream of the positive displacement blower 43, respectively, and the detected pressures and temperature measured by thermocouple 39 are used in calculation of the volumetric flow rate of the total (mixed sample/makeup) gas flow through the blower 43.

A controller, e.g., a microprocessor 60, depicted in FIG. 3, receives, the exhaust flow rate from the flow meter 2 and computes the sample flow rate based on the desired percentage of exhaust flow rate. The controller 60 also calculates the makeup air flow using the thermocouple 21, absolute pressure sensor 23 and the delta pressure sensor 25 and the calibration curve of the LFE 24 and the total flow through the blower 43 using the thermocouple 39 and absolute pressure sensors 37 and 45.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be within the scope of the claims.

We claim:

1. An apparatus for capturing components of interest from vehicle exhaust gas, comprising:
a device for determining exhaust gas flow rate;

a sample tube for capturing a sample of exhaust from an operating vehicle and introducing the captured sample into a sample line;
a resin column connected to the sample line for receiving the exhaust gas sample and selectively capturing the components of interest on the resin, with a residual exhaust gas flow exiting the resin column;
a makeup air line for adding makeup air to the residual exhaust gas flow at a junction downstream of the resin column;
a laminar flow element for receiving a flow of makeup air introduced into the makeup air line and measuring the flow rate of the makeup air;
a proportional control valve for controlling the makeup air flow rate;
a blower for drawing the sample through the sample line, the makeup air through the makeup air line and the combined sample and makeup air through a blower inlet line;
associated with the blower, pressure sensors in the blower inlet line and downstream of the blower and a temperature sensor; and
a controller for calculating the makeup air flow rate and blower flow rate through the blower, based on signals from the temperature and pressure sensors associated with the blower, and controlling the proportional control valve to indirectly regulate the sample flow rate, taken as the blower flow rate minus the makeup air flow rate, as a set percentage of the exhaust gas flow rate.

2. The apparatus of claim 1 further comprising an ice bath in which the resin column is contained.

3. A process for capturing components of interest from vehicle exhaust gas comprising:

capturing a sample of exhaust gas from an operating vehicle;
passing the captured sample through a resin column and selectively capturing the components of interest on the resin with a residual exhaust gas flow exiting the resin column;
adding makeup air to the residual exhaust gas flow at a junction downstream of the resin column;
measuring the flow rate of the makeup air utilizing a laminar flow element;
utilizing a blower, drawing the sample through the sample line, the makeup air through the makeup air line and a combination gas stream of the sample and makeup air through a blower inlet line;
detecting inlet temperature and pressure of the combination gas stream in the blower inlet line;
detecting outlet pressure of the combination gas stream exiting the blower;
calculating the makeup air flow rate based on signals from temperature and pressure sensors associated with the laminar flow element;
calculating the blower flow rate based on signals from the detected inlet temperature and pressure and the detected outlet pressure; and
controlling the proportional control valve to regulate the sample flow rate taken as the blower flow rate minus the makeup air flow rate.

4. The process of claim 3 further comprising determining the flow rate of the exhaust gas and wherein the proportional control valve is controlled to provide a sample flow rate which is a predetermined proportion of the determined flow rate of the exhaust gas.

* * * * *